(12) United States Patent
Killion

(10) Patent No.: US 7,837,005 B2
(45) Date of Patent: Nov. 23, 2010

(54) MUSHROOM-SHAPED PUSH-IN FOAM EARTIP FOR USE WITH HIGH-FIDELITY INSERT EARPHONES

(75) Inventor: Mead C. Killion, Elk Grove Village, IL (US)

(73) Assignee: Etymotic Research, Inc., Elk Grove Village, IL (US)

( * ) Notice: Subject to any disclaimer, the term of this patent is extended or adjusted under 35 U.S.C. 154(b) by 258 days.

(21) Appl. No.: 11/726,124

(22) Filed: Mar. 21, 2007

(65) Prior Publication Data

US 2007/0240931 A1  Oct. 18, 2007

Related U.S. Application Data

(60) Provisional application No. 60/784,244, filed on Mar. 21, 2006.

(51) Int. Cl.
*H04R 25/00* (2006.01)
(52) U.S. Cl. .......................... 181/129; 181/130; 181/131
(58) Field of Classification Search .................. 181/129, 181/130, 131, 135, 137
See application file for complete search history.

(56) References Cited

U.S. PATENT DOCUMENTS

| 3,169,600 A | * | 2/1965 | Thomas ...................... 181/135 |
| 4,006,796 A | * | 2/1977 | Coehorst ..................... 181/130 |
| RE29,487 E | | 12/1977 | Gardner, Jr. |
| 4,677,679 A | | 6/1987 | Killion |
| 4,763,753 A | | 8/1988 | Killion |
| 4,867,149 A | | 9/1989 | Falco |
| 5,002,151 A | * | 3/1991 | Oliveira et al. .............. 181/130 |
| 5,188,123 A | | 2/1993 | Gardner, Jr. |
| 5,887,070 A | | 3/1999 | Iseberg et al. |
| 6,056,698 A | | 5/2000 | Iseberg et al. |
| 6,299,584 B1 | | 10/2001 | Iseberg |
| 6,695,093 B1 | | 2/2004 | Falco |
| 6,702,758 B2 | | 3/2004 | Iseberg |
| 7,314,047 B2 | | 1/2008 | Falco |
| 7,370,655 B2 | | 5/2008 | Taylor |
| 7,475,686 B2 | | 1/2009 | Knauer et al. |
| 2003/0051939 A1 | * | 3/2003 | Werblud ..................... 181/131 |
| 2006/0138691 A1 | | 6/2006 | Knauer et al. |
| 2006/0141083 A1 | | 6/2006 | Knauer et al. |
| 2007/0089755 A1 | | 4/2007 | Knauer |
| 2008/0093158 A1 | | 4/2008 | Taylor |
| 2008/0173315 A1 | | 7/2008 | Falco |
| 2008/0207790 A1 | | 8/2008 | Knauer et al. |

* cited by examiner

*Primary Examiner*—Jeffrey Donels
*Assistant Examiner*—Forrest M Phillips
(74) *Attorney, Agent, or Firm*—McAndrews, Held & Malloy, Ltd.

(57) ABSTRACT

Certain embodiments of the invention may be found in a push-in eartip assembly. The push-in eartip assembly may include a mushroom-shaped foam tip. The push-in eartip assembly may also include a hollow tube extending through the center of the mushroom-shaped foam tip. An inner diameter of the hollow tube may be constant and an outer diameter of the hollow tube may be tapered. In certain embodiments, the push-in eartip assembly may further include an adhesive for bonding the mushroom-shaped foam tip to an outer surface of the hollow tube. In certain embodiments, the hollow tube may extend through a center hole in the mushroom-shaped foam tip that extends from the top to the base of the mushroom-shaped foam tip.

17 Claims, 2 Drawing Sheets

US 7,837,005 B2

MUSHROOM-SHAPED PUSH-IN FOAM EARTIP FOR USE WITH HIGH-FIDELITY INSERT EARPHONES

CROSS-REFERENCE TO RELATED APPLICATIONS/INCORPORATION BY REFERENCE

The present application claims priority under 35 U.S.C. §119(e) to provisional application Ser. No. 60/784,244, filed on Mar. 21, 2006, the entire contents of which are hereby expressly incorporated herein by reference.

FIELD OF THE INVENTION

Certain embodiments of the invention relate to eartips for earphones. More specifically, certain embodiments of the invention relate to a mushroom push-in foam eartip for use with high fidelity insert earphones.

BACKGROUND OF THE INVENTION

Foam eartips can be generally used with earphones for hearing testing, for stereo earphones, and for cellphone earphones. The slow recovery "yellow foam" E-A-R Classic® Earplugs described in U.S. Pat. Re. 29,487 (1977) has been the basis for hundreds of millions of successful solid foam earplugs used for hearing protection, sold by AEARO Corporation of Indiana. Since 1984, Etymotic Research has supplied ER-3 earphones for hearing testing as described in U.S. Pat. No. 4,763,753 (1988) with foam eartips into which a central hollow tube member has been inserted to allow the sound to be transmitted to the ear canal. This latter construction was also described in U.S. Pat. Re. 29,487. FIG. 1 illustrates an exemplary foam eartip with a central hollow tube inserted therein.

Etymotic Research has also supplied the ER-4 and ER-6 insert earphones (U.S. Pat. Nos. 4,677,679, 4,763,753 and 5,887,070) using similar foam eartips, as well as flanged eartips such as described in U.S. Pat. No. 4,867,149 (1989) and also sold by AEARO as their Ultra-Fit® earplugs. FIG. 2 illustrates an exemplary flanged eartip.

The foam eartip may have approximately 5 dB greater external noise attenuation than the flanged eartip. Additionally, the foam eartip may accommodate a greater range of ears that it can fit, and many users report the foam eartip to be more comfortable than the flanged eartip. However, the foam eartip must be rolled down before being inserted; whereas, a flanged eartip can be simply pushed into the ear canal.

In 1993, AEARO introduced a two-part "mushroom tip" foam earplug under the brand name Push-Ins™ and described in U.S. Pat. No. 5,188,123 (1993). By incorporating a relatively stiff solid plastic center member into the core of a shaped foam earpiece, the Push-Ins™ eartips do not require that the foam be rolled down before inserting it. When slowly pushed into the ear canal, the foam compresses during insertion. Despite the ease of insertion, however, the mushroom tip earplug provides nearly as great attenuation as the classic foam eartip. FIG. 3 illustrates an exemplary two-part mushroom tip foam earplug.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A mushroom-shaped push-in foam eartip assembly is provided, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Certain embodiments of the present invention may be found in eartips for earphones. More specifically, the present invention relates to a mushroom-shaped push-in foam eartip for use with high fidelity insert earphones.

Figure 1:
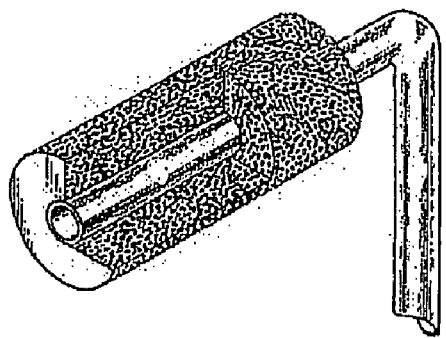
FIG. 1 illustrates an exemplary foam eartip with a central hollow tube inserted therein.
Figure 2:
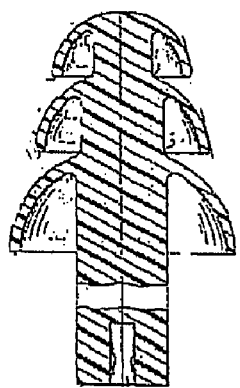
FIG. 2 illustrates an exemplary flanged eartip.
Figure 3:
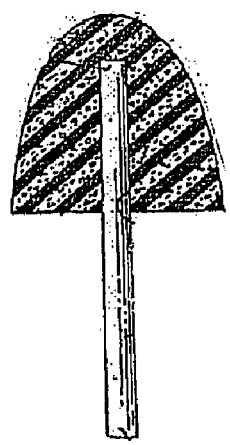
FIG. 3 illustrates an exemplary two-part mushroom tip foam earplug.
Figure 4:
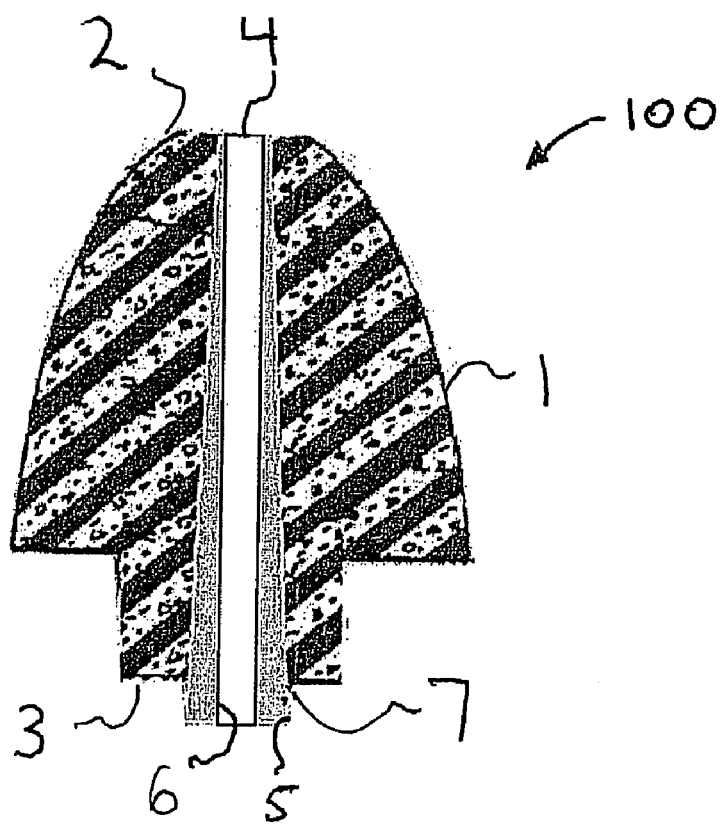
FIG. 4 illustrates an exemplary mushroom-shaped push-in foam eartip, in accordance with an embodiment of the present invention.

FIG. 4 illustrates an exemplary mushroom-shaped push-in foam eartip, in accordance with an embodiment of the present invention. The mushroom-shaped push-in foam eartip 100, may comprise the mushroom-shaped foam tip 1 having a top 2 and a base 3. The mushroom-shaped foam tip 100 may also include a center hole that extends from the top 2 to the base 3 in the mushroom-shaped foam tip 1. The center hole in the mushroom-shaped foam tip 1 may be tapered. In an embodiment, a tapered tube 4 having a constant inner diameter 6 but a tapered outer diameter 5 may extend through the center hole in the mushroom-shaped foam tip 1. The tapered tube 4 may allow greater overall rigidity without increasing the diameter in the portion of the foam placed deep in the ear. In an embodiment, the tapered tube 4 may be a sound tube.

In an embodiment, the outer surface of the tapered tube 4 may be bonded in the center hole of the mushroom-shaped foam tip 1 using an adhesive 7. The adhesive 7 may be a room temperature vulcanizing (RTV) silicone rubber adhesive, among other things. When the complete sound tube eartip is attached to an insert earphone such as, for example, the Etymotic Research ER-4, the earphone-eartip combination may be pushed into the ear as if it were a triple flange eartip. The result is a much greater ease of insertion than possible with a classic foam eartip, combined with a greater attenuation than provided by a triple flange eartip.

With traditional E-A-R foam cylinder eartips, a polyvinyl chloride (PVC) tube can be cemented into a hole through the center. Although numerous foam eartips have been successfully fabricated with this technique, simply using a straight-walled PVC tube cemented into a hole punched in the mushroom-shaped push-in foam eartips may be useable but not as satisfactory in terms of performance. Because of the non-uniform shape of the foam, a tapered silicon tube provided superior results, particularly when used with RTV silicone adhesive. The adhesive forms an excellent bond with the silicon-tapered tube, and also with the semi-porous foam in the mushroom eartip. A bond along the entire length of the tapered tube may be formed to avoid the eartip pulling back during insertion (which now puts much more shear force on the glue bond than pre-rolled cylindrical foam eartips), or separating at the earphone end when the eartip is placed on the earphone.

Another area where improved earplugs may be used is otoacoustic emission testing equipment such as the Ero-Scan equipment, described in U.S. Pat. Nos. 6,299,584, 6,702,758, 6,056,698. The probe tip is normally sealed in the ear through a single flange eartip such as made by Grason. Many technicians who insert the flanged earplug may not do a good job of getting it sealed and may be unwilling or untrained to roll the foam. In such situations, substitution of the new mushroom eartip as described by the present invention may solve the problem.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A push-in eartip assembly, comprising:
    a mushroom-shaped compressible foam tip comprising a center hole extending from a top to a base of the mushroom-shaped compressible foam tip, and
    a hollow tube extending through the center hole of the mushroom-shaped compressible foam tip, wherein an inner diameter of the hollow tube is constant and an outer diameter of the hollow tube is tapered,
    wherein the outer diameter of the hollow tube comprises a narrow end towards the top of the mushroom-shaped compressible foam tip and a wide end towards the base of the mushroom-shaped compressible foam tip.

2. The assembly of claim 1 further comprising an adhesive for bonding the mushroom-shaped compressible foam tip to an outer surface of the hollow tube.

3. The assembly of claim 2 wherein the adhesive is a room temperature vulcanizing (RTV) silicone rubber adhesive.

4. The assembly of claim 1 wherein the center hole in the mushroom-shaped compressible foam tip is tapered.

5. The assembly of claim 1 wherein the hollow tube is made of silicon.

6. The assembly of claim 1 wherein the hollow tube is a sound tube.

7. A push-in eartip apparatus, comprising:
    a hollow tube comprising an inner surface, an outer surface, a narrow end, and a wide end, wherein the inner surface of the hollow tube has a constant diameter and the outer surface of the hollow tube has a tapered diameter; and
    a mushroom-shaped compressible foam tip comprising a top and a base, wherein the hollow tube extends through a center hole in the mushroom-shaped compressible foam tip that extends from the top to the base,
    wherein the narrow end of the hollow tube is towards the top of the mushroom-shaped compressible foam tip and the wide end of the hollow tube is towards the base of the mushroom-shaped compressible foam tip.

8. The apparatus of claim 7 further comprising an adhesive for bonding the mushroom-shaped compressible foam tip to the outer surface of the hollow tube.

9. The apparatus of claim 8 wherein the adhesive is a room temperature vulcanizing (RTV) silicone rubber adhesive.

10. The apparatus of claim 7 wherein the center hole in the mushroom-shaped compressible foam tip is tapered.

11. The apparatus of claim 7 wherein the hollow tube is made of silicon.

12. The apparatus of claim 7 wherein the hollow tube is a sound tube.

13. A push-in eartip assembly, comprising:
    a mushroom-shaped compressible foam tip comprising a top and a base, wherein a center hole in the mushroom-shaped compressible foam tip extends from the top to the base;
    a hollow tube comprising an inner surface and an outer surface, wherein the inner surface of the hollow tube has a constant diameter and the outer surface of the hollow tube has a tapered diameter; and
    an adhesive for bonding the outer surface of the hollow tube in the center hole of the mushroom-shaped compressible foam tip,
    wherein the outer surface of the hollow tube comprises a narrow end bonded towards the top of the mushroom-shaped compressible foam tip and a wide end bonded towards the base of the mushroom-shaped compressible foam tip.

14. The assembly of claim 13 wherein the adhesive is a room temperature vulcanizing (RTV) silicone rubber adhesive.

15. The assembly of claim 13 wherein the center hole in the mushroom-shaped compressible foam tip is tapered.

16. The assembly of claim 13 wherein the hollow tube is made of silicon.

17. The assembly of claim 13 wherein the hollow tube is a sound tube.

* * * * *